(12) United States Patent
Choi et al.

(10) Patent No.: US 8,340,758 B2
(45) Date of Patent: Dec. 25, 2012

(54) METHOD AND APPARATUS FOR CONTROLLING ELECTRICAL STIMULATION

(75) Inventors: Charles Tak Ming Choi, Hsinchu (TW); Chien Hua Hsu, Zhubei (TW)

(73) Assignee: National Chiao Tung University, Hsinchu (TW)

( * ) Notice: Subject to any disclaimer, the term of this patent is extended or adjusted under 35 U.S.C. 154(b) by 771 days.

(21) Appl. No.: 12/358,539

(22) Filed: Jan. 23, 2009

(65) Prior Publication Data
US 2009/0248110 A1 Oct. 1, 2009

(30) Foreign Application Priority Data
Mar. 28, 2008 (TW) ............................... 97111262 A (51) Int. Cl.
*A61N 1/00* (2006.01)
(52) U.S. Cl. ................ 607/2; 307/57; 307/59
(58) Field of Classification Search .......... 607/2, 55–57, 607/59, 62, 46
See application file for complete search history.

(56) References Cited

U.S. PATENT DOCUMENTS
6,393,325 B1  5/2002  Mann et al.
2004/0136556 A1  7/2004  Litvak et al.

OTHER PUBLICATIONS

Miyoshi, S. et al., "Proposal of a New Method for Narrowing and Moving the Stimulated Region of Cochlear Implants: Animal Experiment and Numerical Analysis", IEEE Transactions on Biomedical Engineering, vol. 46, No. 4, Apr. 1999, pp. 451-460.

*Primary Examiner* — Scott Getzow
(74) *Attorney, Agent, or Firm* — Bui Garcia-Zamor; Hung H. Bui, Esq.

(57) ABSTRACT

An apparatus and method for controlling an electrical stimulation system to increase the resolution of the stimulation region with multiple independent power source electrodes is proposed. In the apparatus, the electrode set contains at least three electrodes of which two adjacent electrodes are of the same power polarity to control the location of the composite stimulation signal and the others are of an inverse power polarity to balance the total power polarity and narrow the stimulation region. The method for the apparatus comprises steps of: receiving a target stimulation location and level, generating at least one parameter to adjust power settings of the electrodes, thereby obtaining a composite stimulation signal corresponding to a virtual channel of which a location and level match the target stimulation location and level.

23 Claims, 10 Drawing Sheets
(7 of 10 Drawing Sheet(s) Filed in Color)

METHOD AND APPARATUS FOR CONTROLLING ELECTRICAL STIMULATION

CROSS-REFERENCE TO RELATED APPLICATION

This application claims all benefits accruing under 35 U.S.C. §119 from Taiwanese Patent Application No. 097111262, filed on Mar. 28, 2008 in the Intellectual Property Office Ministry of Economic Affairs, Republic of China, the disclosure of which is incorporated by reference herein.

TECHNICAL FIELD

The invention relates to a method and apparatus for controlling electrical stimulation, and more particularly to a method and apparatus for controlling electrical stimulation by using a plurality of electrodes to focus the stimulation regions of virtual channels.

BACKGROUND OF THE INVENTION

Currently, the electrodes applied for stimulating nerve fibers are unable to be made as small as individual nerve fibers. In prior arts, the nerves in the proximity of the electrodes can be stimulated, but some nerves located between the electrodes are unable to be stimulated. Because the number of electrodes determines the number of perceptual channels in prior arts, it not only leads to low stimulation resolution, but also fails to stimulate some of the nerves.

The electrodes, mediums for delivering electrical charges to stimulate nerve fibers and to reconstruct a normal hearing transmission pathway, often fail to cover and clearly distinguish all the nerve fibers due to its physical dimension. Moreover, the stimulation resolution and the actual perceived information is degraded. For example, even if 16-22 electrodes are implanted into a cochlear implant user, there are approximately 30,000 auditory nerve fibers in a typical normal ear and less for a typical hearing impaired ear and only auditory nerve fibers in the proximity of the electrodes could be stimulated. Therefore, the hearing perception quality of cochlear implant users is degraded due to low stimulation coverage and low spatial stimulation resolution. At present, there are a certain number of languages can afford lower stimulation resolution and bandwidth in relatively quiet environment, the cochlear implant is able to assist patients using such languages. However, for tonal languages such as the Mandarin Chinese and Cantonese Chinese, the cochlear implant users often cannot clearly distinguish the tones of the words and understand what they hear. More importantly, music cannot be fully captured by a typically cochlear implant system and noisy environment would impede the users' hearing quality further.

Generally, electrical stimulation generated by an electrode is carryout by applying a current or voltage to at least one physical electrode, so as to generate an electrical stimulation signal in the electrode, and subsequently stimulate nerve fibers in the proximity of the electrode. Recently, it is proposed to use the so-called virtual electrode or virtual channel technology to improve the hearing resolution without the need to increase the original number of implanted electrodes. The generation of the virtual electrode or virtual channel is mainly achieved by adjusting the current ratio of at least two electrodes, so as to generate a stimulation signal between the two electrodes. In other words, current levels of two adjacent electrodes are adjusted by current control so as to generate an intermediate channel (stimulation) between the two adjacent electrodes. Since no physical electrode is present between the two electrodes, the generated intermediate stimulation signal is called the virtual electrode or virtual channel. Therefore, it is possible to generate electrical stimulation signal and stimulation sites that exceeds the number of the physical electrodes, so as to stimulate more nerve fibers located between the electrodes, thereby improving the resolution of stimulation and the hearing quality of cochlear implant users. Moreover, the power sources of the electrodes can be configured as current sources or voltage sources.

The virtual channel technology is mainly achieved by adjusting a ratio of power setting of two electrodes and can be found in U.S. Patent Publication No. 2004/0136556 published on Jul. 15, 2004. In U.S. Patent Publication No. 2004/0136556, it is disclosed that a plurality of electrodes of an identical power polarity are actuated by adjusting a current ratio of the electrodes to a reference electrode or a ground electrode of an inverse power polarity with respect to the electrodes of the identical power polarity for balancing a total power polarity. This type of stimulation is called monopolar stimulation. However, the beamwidth of the electrical stimulation signal resulted from monopolar stimulation is so wide that it is difficult to focus the stimulation, and the number of distinguishable virtual channels is not sufficient to improve the resolution of hearing frequency.

In the April issue of IEEE Transactions on Biomedical Engineering of 1999, a paper titled "Proposal of a New Method for Narrowing and Moving the Stimulated Region of Cochlear Implants: Animal Experiment and Numerical Analysis" was proposed by Shigeki et al. In summary, Shigeki and colleagues proposed a method that uses a virtual electrode generated by three adjacent electrodes (wherein a total current of two lateral electrodes is equal to the current of the central electrode) to narrow down stimulation regions, and a stimulation location is moved by adjusting parameters of the two lateral electrodes. This method is capable of narrowing down the stimulation signal (beamwidth) by adjusting the parameters of the two lateral electrodes. However, by this type of electrical stimulation apparatus, only the nerve fibers in the proximity of the central electrode is able to be stimulated, that is, the apparatus has an effective stimulation range restricted to the vicinity of the central electrode and is incapable of sufficiently moving the location of the virtual channel or stimulation sites between the electrodes. As a result, this virtual electrode cannot be used to stimulate the nerve fibers located between the two electrodes, and hence the stimulation resolution of the signal is not improved effectively.

Although the prior art US2004/0136556 had implied an idea of combining multiple electrodes for generating a virtual channel, no specific implementation was proposed, and the use of multiple electrodes for adjusting the virtual channel would be technically more complicated than using only two electrodes. In addition, regardless of how many electrodes are used to generate the virtual channel in the prior art US2004/0136556, an additional external reference electrode (or grounding electrode) is still required to balance the total power polarity of the electrode set. It is costly, and the efficiency of electrodes usage would be degraded.

SUMMARY OF INVENTION

To solve the aforesaid technical disadvantages and allow users to receive better stimulation resolution and allow the cochlear implant users to attain hearing performance approximating to or matching the users' original hearing functions, a method and apparatus for controlling electrical stimulation are proposed which improve the focus of electrical stimulation by simply adjusting multiple power settings of electrodes, so as to focus the beamwidth of the virtual channel in order to improve the electrical stimulation resolution of the nerves.

A primary object of the invention is to provide an apparatus for controlling electrical stimulation to stimulate nerve fibers, which comprises an electrode array and an electrode controller. A virtual channel is created by adjusting the power settings of two adjacent electrodes of the first power polarity in the electrode array and power settings of the other electrodes of the second power polarity which is inverse with respect to the first power polarity.

Another object of the invention is to provide a method for controlling electrical stimulation by using a plurality of electrodes for stimulating nerve fibers. A location of a virtual channel is moved by adjusting parameters of power settings of the electrodes.

Another object of the invention is to provide a method for controlling electrical stimulation by using a plurality of electrodes for stimulating nerve fibers. Power settings of an electrode set to be driven in an electrode array is adjusted, thereby obtaining a composite stimulation signal corresponding to a virtual channel of which the location and level are equal or similar to a target stimulation location and level.

Another object of the invention is to provide an apparatus for controlling electrical stimulation for stimulating nerve fibers, which comprises an electrode array and an electrode controller. The electrode array comprises an electrode set composed of a plurality of electrodes each of which is powered and controlled by an independent power source. The electrodes of the electrode set are so configured that at least one of the electrodes is of the first power polarity and the others of the electrodes is of the second power polarity which is inverse with respect to the first power polarity. A virtual channel is moved by adjusting power settings of the electrode set.

A further object of the invention is to provide a method and apparatus for controlling electrical stimulation for stimulating nerve fibers, which may be applied to a cochlear implant, retinal prosthesis, spinal cord stimulation apparatus, and deep brain stimulation apparatus.

BRIEF DESCRIPTION OF DRAWINGS

The patent or application file contains at least one drawing executed in color. Copies of this patent or patent application publication with color drawing(s) will be provided by the Office upon request and payment of the necessary fee.

DETAILED DESCRIPTION OF PREFERRED EMBODIMENTS

Figure 1:
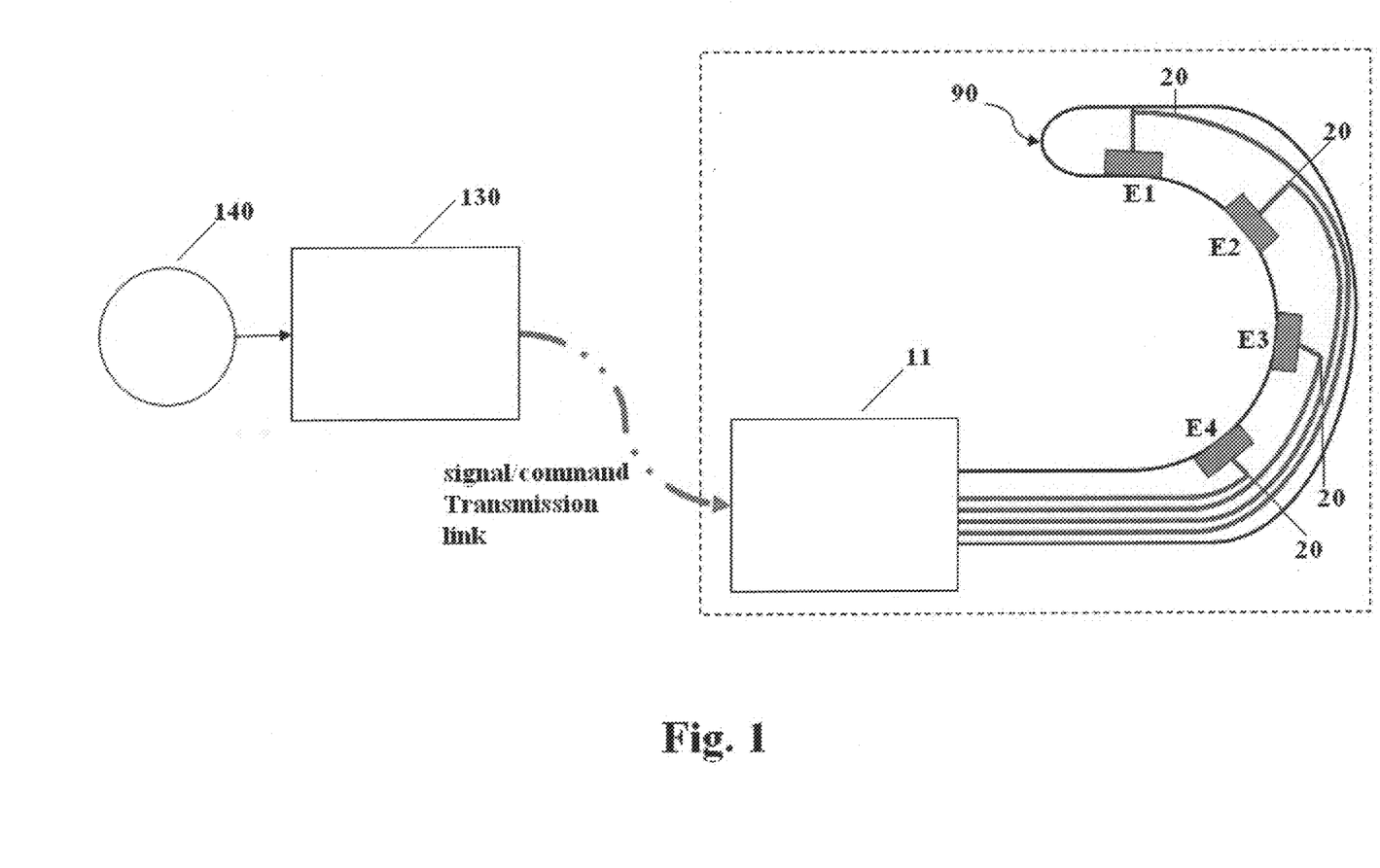
FIG. 1 shows an apparatus for controlling electrical stimulation used for stimulating nerve fibers according to the invention.

Referring to FIG. 1, FIG. 1 shows an apparatus for controlling electrical stimulation used for stimulating nerve fibers according to the invention. In addition to a basic configuration of a general electrical stimulation apparatus such as an input module 140, a stimulation processor 130, and wired or wireless signal/command transmission connections, the apparatus also comprises: an electrode array 90 having a plurality of electrodes (indicated as E1~E4 in FIG. 1) each of which is separately powered and controlled by an independent power source 20; and an electrode controller 11 for receiving input control signals and driving an electrode set (comprised of a plurality of electrodes), so as to generate a composite stimulation signal (i.e. a virtual channel) in the electrode set. The electrode set includes at least three electrodes, wherein two adjacent electrodes are of the first power polarity and can be used to control the location of the composite stimulation signal, while the other electrode is of the second power polarity which is inverse with respect to the first power polarity, so as to balance the total power and charge polarity and focus on a stimulation region. Because the electrode set has at least one electrode of the second power polarity for balancing the total power polarity, stimulation resulted from the electrode of the first power polarity can be balanced, thereby reducing beamwidth of the resulted virtual channel and making the virtual channel more focused.

The electrode set may also be comprised of four or more electrodes, wherein at least one of the electrodes is of the first power polarity and the other electrodes are of the second power polarity which is inverse with respect to the first power polarity. By adjusting the power settings of the electrodes, the virtual channel is focused more than that generated by two or three electrodes.

According to the invention, at least one electrode of the electrodes may be used to balance the total power polarity of the electrode set. Therefore, an additional ground electrode is unnecessary for balancing the total power polarity of the electrode set. Electrical stimulation generated according to this invention may be bipolar stimulation, tripolar stimulation, quadrapolar stimulation, or multipolar stimulation which is generated by more electrodes than four. Moreover, the virtual channel may be generated in order to increase resolution of stimulation by proportionally adjusting the stimulation currents of at least two electrodes without increasing the number of the total electrodes.

Figure 2:
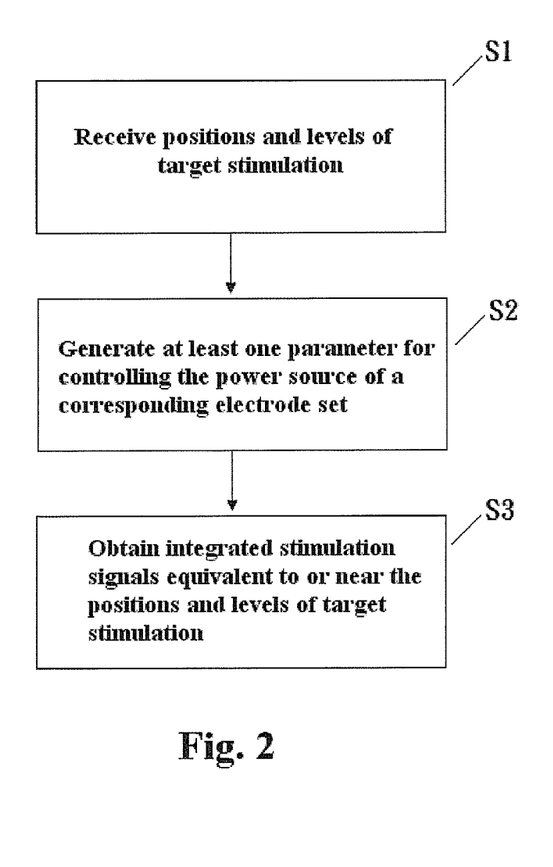
FIG. 2 is a flow chart of the method for controlling electrical stimulation used for stimulating nerve fibers according to the invention.

Referring to FIG. 2, FIG. 2 is a flow chart of the method for controlling electrical stimulation used for stimulating nerve fibers according to the invention. The method for controlling electrical stimulation includes the following steps: receiving a target stimulation location and level (step S1); and generating at least one parameter for adjusting power settings of a electrode set (step S2), and obtaining a composite stimulation signal corresponding to a virtual channel of which the location and level match the target stimulation location and level (step S3). The electrode set includes at least three electrodes, in which two adjacent electrodes are of the first power polarity and are used for controlling the target location of the composite stimulation signal, while the other electrode is of the second power polarity which is inverse with respect to the first power polarity, so as to balance a total power polarity and focus on a stimulation region.

The invention has also provided another method for controlling electrical stimulation with a plurality of electrodes for stimulating nerve fibers, which comprises the following steps: receiving a target stimulation location and level; generating at least one parameter for adjusting power settings of an electrode set, thereby obtaining a composite stimulation signal corresponding to a virtual channel of which a location and level match the target stimulation location and level. The electrode set includes a plurality of electrodes for controlling the target location of the composite stimulation signal. At least one of the electrodes is of the first power polarity and the other electrodes are of the second power polarity which is inverse with respect to the first power polarity, so as to balance the total power polarity and focus on a stimulation region by controlling the power settings of the electrodes.

A method is further proposed for simplifying a plurality of parameters into a single parameter and hence effectively simplifies the complexity of clinical trials. Generally, the actual operation of the apparatus can be made easier and time-saving by controlling the current ratio of the electrodes and by the simplification of the procedures.

The invention allows cochlear implant users to receive improved hearing perception by increasing the frequency resolution of the stimulation, and may also be applied to other fields related to the electrical nerve stimulation apparatus, such as retinal prosthesis, spinal cord stimulation, and deep brain stimulation.

Figure 3:
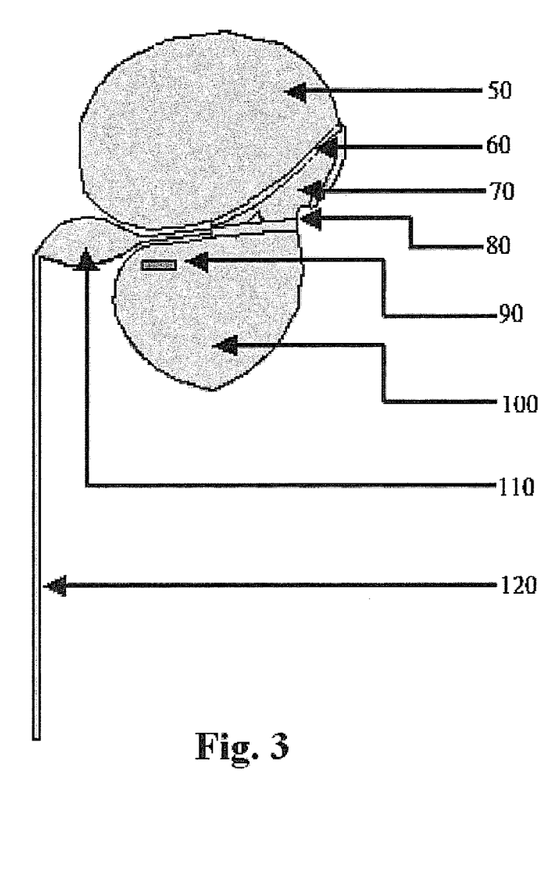
FIG. 3 schematically illustrates a cross section of a human cochlea.
Figure 4:
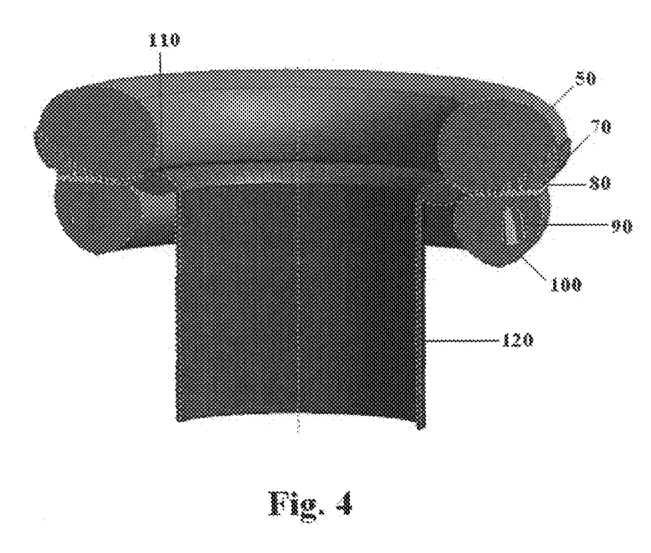
FIG. 4 is a partial 3D model of a human cochlea wherein the half turn of the human cochlea is shown.
Figure 5:
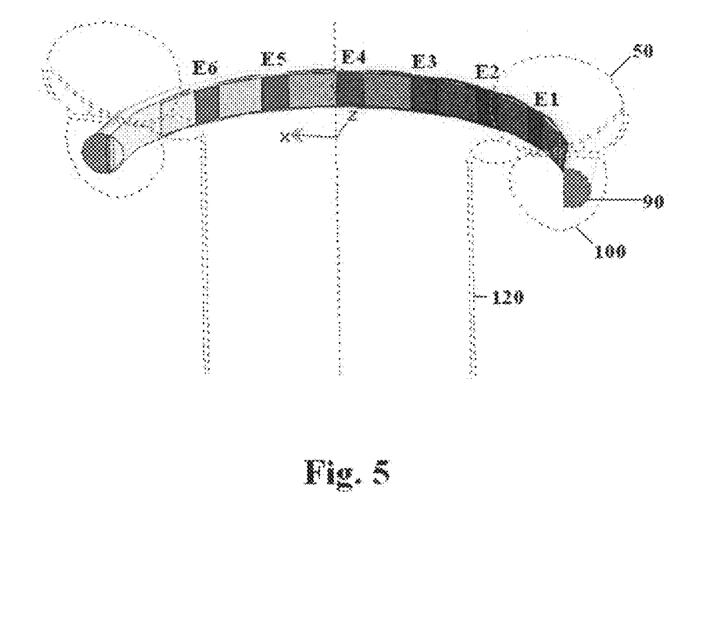
FIG. 5 is a perspective view showing an electrode array disposed in the model of FIG. 4.

According to the invention, the electrical stimulation signal for the auditory nerves of the human cochlea is simulated by modeling. In FIGS. 3 and 4, a cross section of a human cochlea and a partial 3D model of the human cochlea are shown. Specifically, FIG. 3 shows the cross section of the human cochlea while FIG. 4 shows the 3D model of a half turn of the human cochlea. The human cochlea model consists of a scala vestibuli 50, a Reissner's membrane 60, a scala media 70, a basilar membrane 80, a scala tympani 100, a group of spiral ganglions 110 and a group of medial axonal processes 120. An electrode array 90 (for example, the 6×1 electrode array shown in FIG. 5) is implanted in the scala tympani 100.

The finite-element method is applied for calculating the potential distribution in the cochlea model so as to calculate activating functions for determining reactions of nerve fibers and obtain auditory impressions by the activating functions. Because peak of the activating functions corresponds to the location where the nerves are most easily stimulated, the peaks may be regarded as the location of the virtual channel.

Figure 6:
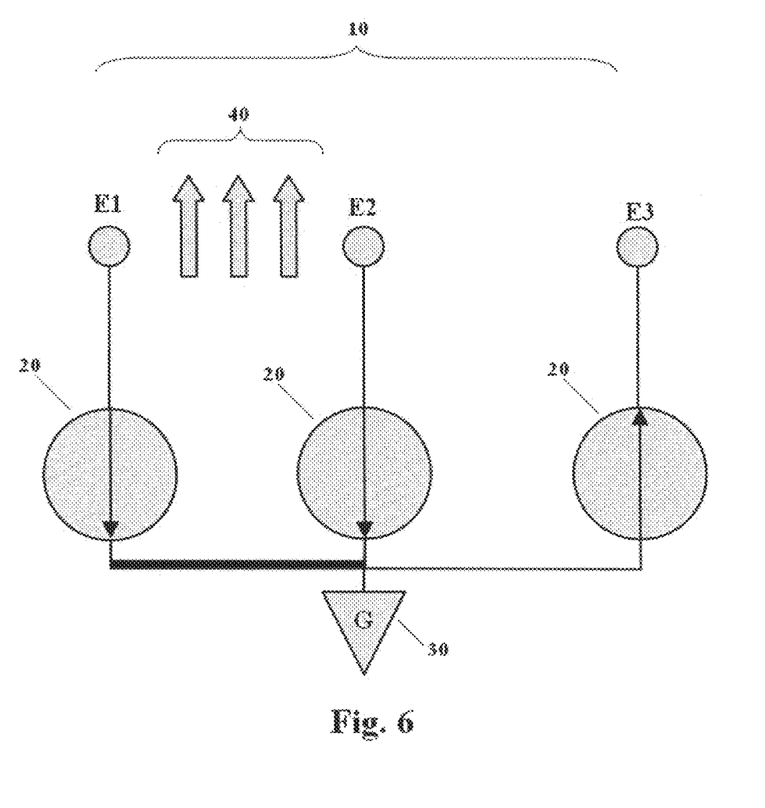
FIG. 6 schematically illustrates an embodiment with three electrodes according to the invention.

FIG. 6 shows the first embodiment with three electrodes according to the invention. An electrode set 10 of the electrode array is configured as one comprising three electrodes (E1~E3) in this embodiment. If the composite stimulation signals 40 (the virtual channels indicated as the arrows between the left and central independent power sources 20 in FIG. 6) are located between two adjacent electrodes (i.e. between E1 and E2) which are of the first power polarity, settings of the power sources 20 of the two electrodes are designated as $(-(1-\alpha))P$ and $(-\alpha)P$, and setting of the power source 20 of the third electrode which is of the second power polarity which is inverse with respect to the first power polarity is designated as P, where P is a total power setting which can be configured as a voltage (V) or a current (I). Alternatively, settings of the power sources 20 of the two electrodes are designated as $(1-\alpha)P$ and $(\alpha)P$ respectively, and setting of the power source 20 of the third electrode is designated as $-P$, where $\alpha$ is a parameter ranging from 0 to 1. A ratio of power settings of the two adjacent electrodes of the first power polarity may be set by adjusting the parameter $\alpha$, thereby controlling the stimulation location of the virtual channel 40. The stimulation location of the virtual channel 40 is moved between the two adjacent electrodes on the left as the parameter $\alpha$ is varied.

In this embodiment, because a total power polarity P (or $-P$) of the two adjacent electrodes on the left and a total power polarity $-P$ (or P) of the electrode on the right are equal in level but have polarities inverse with respect to each other, the total power polarity of the electrode set 10 is balanced. Similarly, in the case (not shown in the drawings) that the two adjacent electrodes on the right (i.e. E2 and E3) are of the first power polarity, and the electrode on the left (i.e. E1) is of the second power polarity which is inverse with respect to the first power polarity, the virtual channel 40 would be generated between the two adjacent electrodes on the right, and the stimulation location of the virtual channel 40 can be moved by adjusting the parameter $\alpha$. Because the actual position of the implanted electrodes depends on users, the location and level that need to be stimulated by the virtual channel 40 may be different by case. Therefore, the virtual channel 40 may be set to an optimal location by adjusting the parameter $\alpha$.

In addition, because the total power polarity of the electrode set 10 may be balanced by setting at least one electrode of the second power polarity in the invention, no additional external electrode is required to serve as ground electrode for balancing the total power polarity. Moreover, because the stimulation signal generated from the electrodes of the second polarity in the electrode set 10 counter each other, the beamwidth of the resulted virtual channel 40 is reduced, thereby generating a more focused virtual channel 40.

Figure 7:
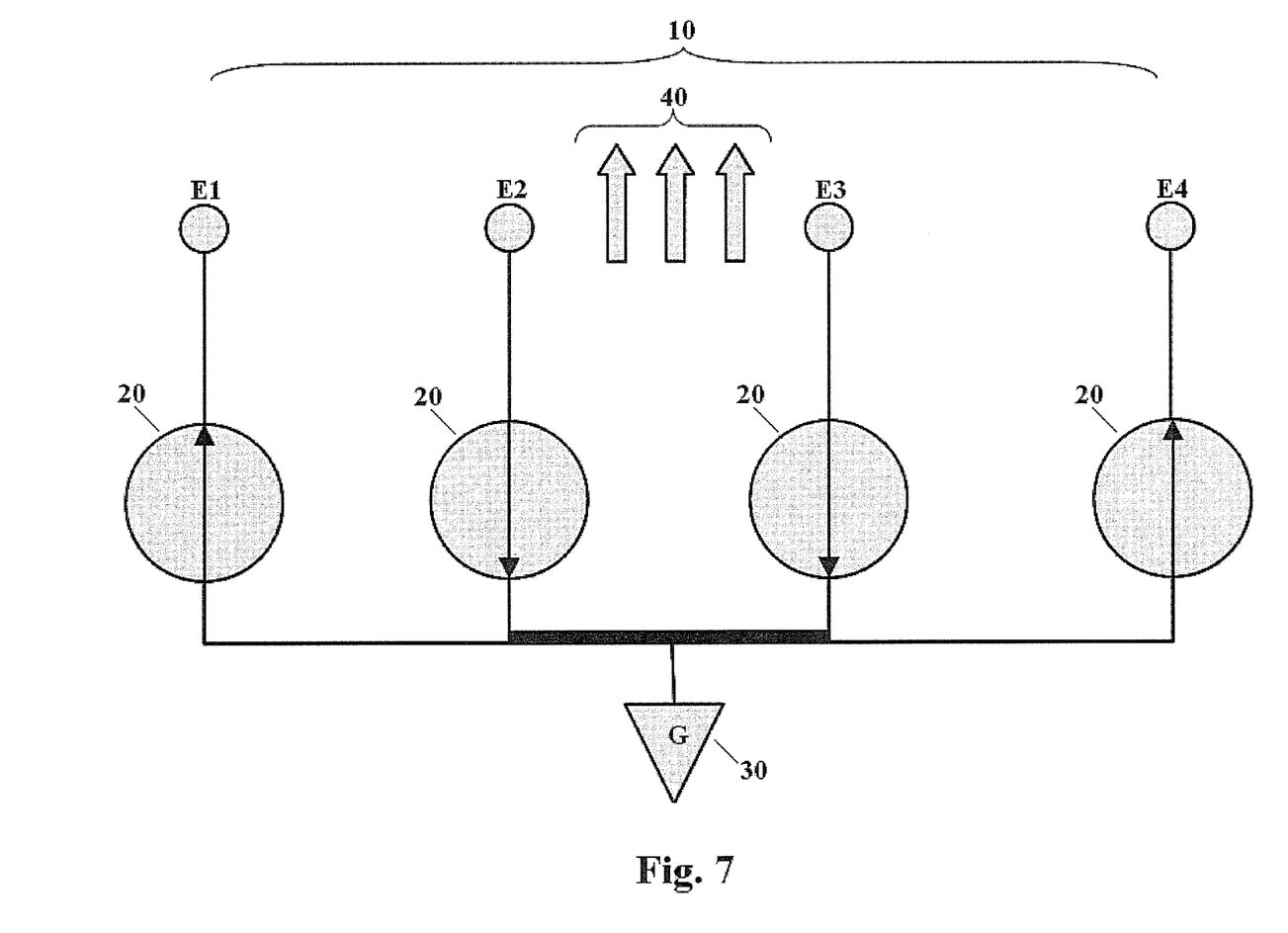
FIG. 7 schematically illustrates an embodiment with four electrodes according to the invention.

FIG. 7 shows the second embodiment with four electrodes according to the invention. An electrode set 10 of the electrode array is configured as one comprising four electrodes (E1~E4) in this embodiment, and two central adjacent electrodes (i.e. E2 and E3) are of the first power polarity with a total power polarity P (or $-P$), while two lateral electrodes (i.e. E1 and E4) are of the second power polarity, which is inverse with respect to the first power polarity, with a total power polarity $-P$ (or P) for balancing the total power polarity of the electrode set 10, where P is a total power setting which can be configured as a voltage (V) or a current (I). In addition, it is possible to control the stimulation location of the virtual channels 40 by adjusting power settings of the two central electrodes. Settings of the power sources 20 of the electrode set 10 may be designated as (from the left to the right): E1=(B)P, E2=$-(1-A)$P, E3=$(-A)$P, and E4=$(1-B)$P, or as: E1=$(-B)$P, E2=$(1-A)$P, E3=$(A)$P, and E4=$(-(1-B))$P; where A and B are parameters ranging from 0 to 1. As the first embodiment, the stimulation location of the virtual channel 40 is moved between the two adjacent electrodes by adjusting the parameters A and B.

In the second embodiment, the two control parameters (A and B) are used for the electrode set 10 with four electrodes so that control of the adjustment of power settings of the electrodes becomes more complicated and difficult. Accordingly, several control schemes (the following five schemes) for simplifying the two control parameters into a single parameter are proposed, which not only reduces the control complexity, but also generates different performance characteristics for the virtual channel. Furthermore, due to the fact that users respond differently to stimulation of the implanted electrodes, it is possible for the users to select their own preferred control schemes, so as to generate the performance characteristics for the virtual channel required by the users. In the following scheme, the parameter α can be adjusted from 0 to 1, while P represents a total power setting:

i. Scheme 1: in the case that both of the parameters A and B are designated as α, settings of the independent power sources 20 of the electrodes may be simplified as: E1=(α)P, E2=−(1−α)P, E3=(−α)P, and E4=(1−α)P, or as: E1=(−α)P, E2=(1−α)P, E3=(α)P, and E4=(−(1−α))P;
  ii. Scheme 2: in the case that the parameters A and B are designated as α and (1−α), respectively, settings of the independent power sources 20 of the electrodes may be simplified as: E1=(1−α)P, E2=−(1−α)P, E3=(−α)P, and E4=(α)P, or as: E1=(−(1−α))P, E2=(1−α)P, E3=(α)P, and E4=(−α)P;
  iii. Scheme 3: in the case that the parameters A and B are designated as α and 0.5, respectively, settings of the independent power sources 20 of the electrodes may be simplified as: E1=(0.5)P, E2=−(1−α)P, E3=(−α)P, and E4=(0.5)P, or as: E1=−(0.5)P, E2=(1−α)P, E3=(α)P, and E4=−(0.5)P;
  iv. Scheme 4: in the case that the parameters A and B are designated as 0.5 and α, respectively, setting of the independent power sources 20 of the electrodes may be simplified as: E1=(α)P, E2=(−0.5)P, E3=(−0.5)P, and E4=(1−α)P, or as: E1=−(α)P, E2=(0.5)P, E3=(0.5)P, and E4=−(1−α)P;
  v. Scheme 5: in the case that the parameters A and B are designated as a corresponding known parameter α in a table Ti and α, respectively, setting of the power sources 20 of the electrodes may be simplified as: E1=(α)P, E2=(−(1−α))P, E3=(−α)P, and E4=(1−α)P, or as: E1=−(α)P, E2=(1−α)P, E3=(α)P, and E4=(−(1−α))P; where the table Ti is a table established according to characteristics of users that correspond to the $i^{th}$ virtual channel, and the table may be established according to the parameters adjustment disclosed in the prior art US2004/0136556 or other prior arts of parameters adjustment for adjusting a current ratio of two electrodes, or according to a length ratio of the $i^{th}$ virtual channel to the two adjacent electrodes; the adjustment parameter α can be used to fine tune the power settings of the two lateral electrodes (such as the electrodes E1 and E4 in this embodiment), so as to more precisely generate a corresponding virtual channel at a desired location for stimulation.

It should be noted that the invention shall not be limited to the above embodiments. Inventions or creations derived from the technical features of the present invention by an ordinarily skilled person in the art would not depart from the present invention and shall fall into the scope of the claimed invention.

The third embodiment of the invention will be described below. In this embodiment, the electrode set of the electrode array is designated as one comprising four electrodes (E1~E4), but it differs from the second embodiment in that the four electrodes in the electrode set are directly represented by the formulas including: E1=(1−α)AP, E2=(2α−1−(αB))P, E3=(1−2α+(αA)−A)P, and E4=(αB)P, where α, A, and B are parameters ranging from 0 to 1. It can be seen that in this embodiment, it is unnecessary that the two central electrodes are designated as the first power polarity and the two lateral electrodes are designated as the second power polarity which is inverse with respect to the first power polarity as the second embodiment. Although three parameters are used for adjustment in this embodiment, the parameters may also be simplified into a single parameter for the adjustment. For example, both of A and B may be designated as 0.5, and then the final power settings may be designated as E1=0.5(1−α)P, E2=(1.5α−1)P, E3=(0.5−1.5α)P, and E4=(0.5α)P; the designation of the power settings depend on α in correspondence with different electrode set. The following Table 1 is an example wherein in the case that the parameters A and B are both designated as 0.5, values for designating power settings of individual electrodes may be obtained by different values of the parameter α.

TABLE 1

|  | E1 | E2 | E3 | E4 |
|---|---|---|---|---|
| α = 0 | 0.5P | −P | 0.5P | 0 |
| α = 0.3 | 0.35P | −0.55P | 0.05P | 0.15P |
| α = 0.4 | 0.3P | −0.4P | −0.1P | 0.2P |
| α = 0.5 | 0.25P | −0.25P | −0.25P | 0.25P |
| α = 0.6 | 0.2P | −0.1P | −0.4P | 0.3P |
| α = 0.7 | 0.15P | 0.05P | −0.55P | 0.35P |
| α = 1 | 0 | 0.5P | −P | 0.5P |

Figure 8:
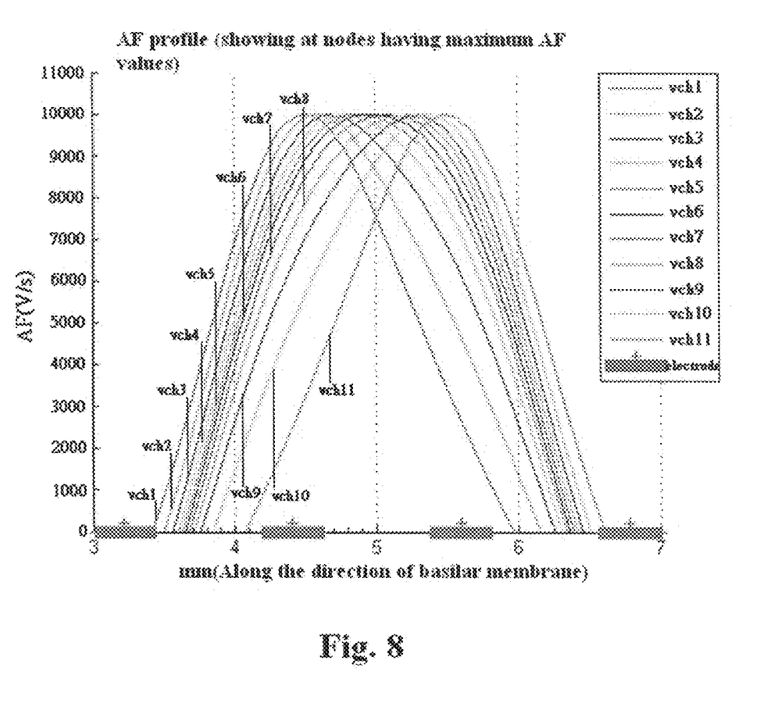
FIG. 8 is a graph of the AF profile generated by the embodiment with four electrodes according to the invention.
Figure 9:
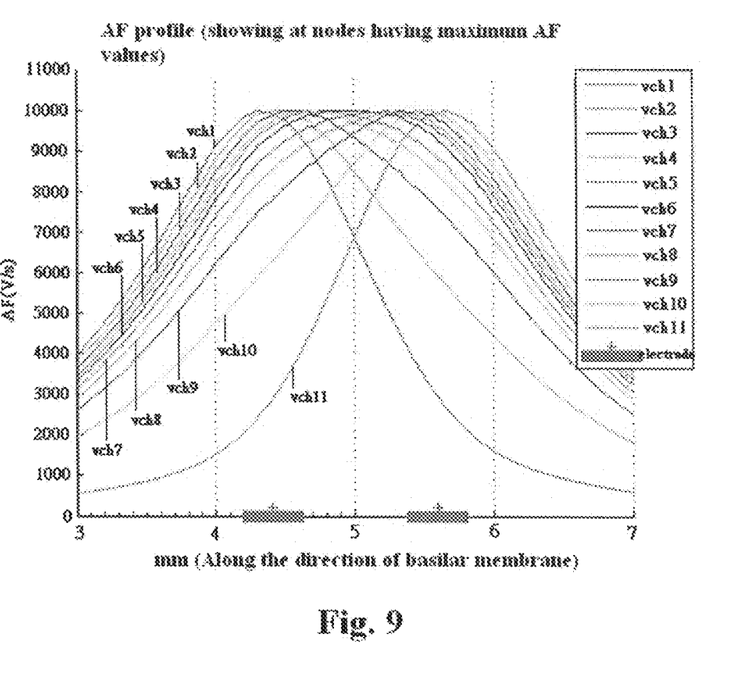
FIG. 9 is a graph of the AF profile generated by the existing stimulation apparatus with two electrodes.

Referring to FIGS. 8 and 9, the AF profiles generated by using four electrodes and two electrodes are compared with each other in order to indicate characteristics of the optimal virtual channel of the invention. FIG. 8 is an AF profile generated from using the third type of the second embodiment (four electrodes) according to the invention while FIG. 9 is an AF profile generated from using two electrodes; wherein vch1~vch11 represent the virtual channels 1 to 11, and the marks  on the X axis are the corresponding electrode contacts denoting the positions along basilar membrane. The AF profiles are obtained by extracting the AF data from AF contours at node with positive peak along the basilar membrane, which means the AF profiles are the nodes that represent the maximum stimulation. By comparing the outcome of simulation from FIG. 8 with FIG. 9, the stimulation regions of the virtual channels generated by using four electrodes for adjustment are more focused than those generated by using two electrodes in the prior art so that the resolution of the stimulation and the resulted hearing perception quality is improved.

Figure 10:
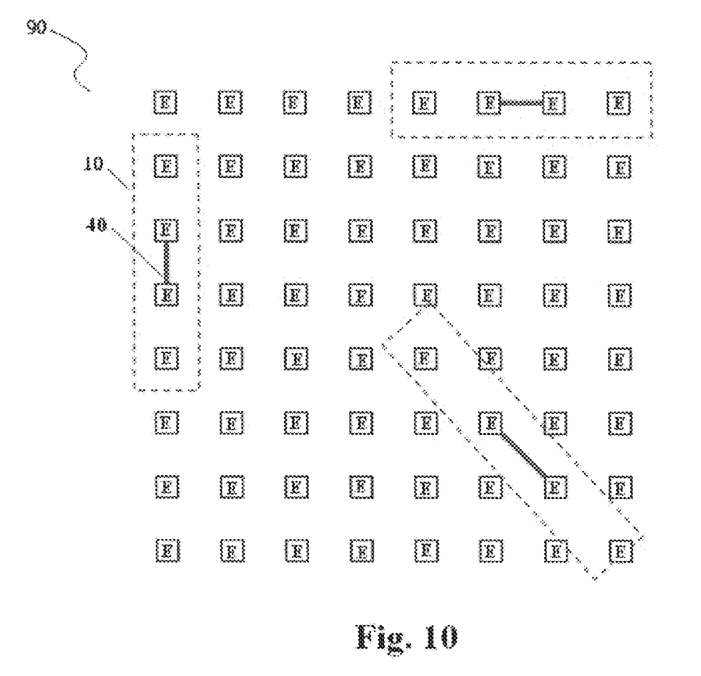
FIG. 10 schematically illustrates an electrode array for retinal prosthesis.

Furthermore, a method and apparatus for controlling electrical stimulation proposed in the invention may also be applied to retinal prosthesis, in which the implementation of the retinal prosthesis also converts the received signals into currents to stimulate optical nerve fibers, so as to reconstruct a normal visual transmission pathway. Referring to FIG. 10, an electrode array of retinal prosthesis is schematically illustrated; wherein each rectangle represents an electrode contact E. The manner for generating virtual channel in a two-dimensional electrode array (for example, an 8×8 electrode array 90) of the retinal prosthesis may be similar to the manner applied in a one-dimensional electrode array such as the above embodiments of the present invention as described with regard to the cochlear implants. In FIG. 10, the dotted squares each indicate an electrode set with four electrodes used to stimulate visual nerves. When the method and apparatus for controlling electrical stimulation according to the invention are applied to retinal prosthesis, the virtual channel 40 would be generated at areas marked with bold lines, thereby improved the visual quality of the users as well.

The spinal cord stimulation and the deep brain stimulation are treatments aimed at suppressing or soothing symptoms and pain by stimulating nerves with electrical currents (by using electrode arrays). The concept thereof is the same as this invention, which focuses the stimulation region of the virtual channel and increases the resolution of the stimulation region, and thus the invention may be applied to the spinal cord stimulation and the deep brain stimulation.

Although the preferred embodiments of the invention have been disclosed above, the invention is not limited to the embodiments. An ordinarily skilled person in the art would appreciate various changes and modifications to the invention without departing from the spirit and scope of the invention. For example, the invention may also be allowed to generate a more focused virtual channel by adjusting the power settings and polarity of five or more electrodes. The input module of the invention may be microphones for cochlear implant, cameras for retinal prostheses or joysticks for spinal cord stimulation. The stimulation processor may be implemented by a digital signal processor (DSP), central processing unit (CPU), microprocessor, arithmetic and logic unit (ALU) or the like. The plurality of parameters used for adjusting power settings of electrodes in this invention may also be generated by other linear formulas or specific formulas. The activating function may also be maximized by using genetic algorithm (GA), so that the electrode array in the scala tympani may be rotated at optimal angles, thereby effectively stimulating the spiral ganglion and the medial axonal process. Therefore, the invention has the full scope permitted by the language of the following claims.

It is noted that the endpoints of a range shall be included in this specification. Therefore, the mentioned range contains the endpoints and any integer and fraction between the endpoints.

What is claimed is:

1. An apparatus for controlling electrical stimulation used for stimulating nerve fibers, comprising:
   an electrode array including an electrode set having a first electrode, a second electrode, a third electrode and a fourth electrode, each of which is separately powered and controlled by an independent power source; and
   an electrode controller for receiving input control signals and driving an electrode set in the electrode array so as to generate a composite stimulation signal in the electrode set;
   wherein the second and third electrodes are adjacent and are of a first power polarity for controlling a location of the composite stimulation signal, and the first and fourth electrodes are of a second power polarity which is inverse with respect to the first power polarity, so as to balance a total power polarity of the electrode set and focus on a stimulation region of the composite stimulation signal which is generated between the second and the third electrodes, and
   wherein the second and third electrodes of the first power polarity have a power setting designated as $(-(1-A))P$ and $(-A)P$, respectively, while the first and fourth electrodes of the second power polarity have a power setting designated as $(B)P$ and $(1-B)P$, respectively, where A and B are parameters ranging from 0 to 1, the location of the composite stimulation signal can be controlled by adjusting the parameters A and B, and P is a total power setting.

2. The apparatus according to claim 1, wherein the parameters A and B are designated so that they are equal to each other.

3. The apparatus according to claim 1, wherein the parameters A and B are designated so that an equation, $A+B=1$, is fulfilled.

4. The apparatus according to claim 1, wherein the parameter A is designated as 0.5 and the parameter B is designated as $\alpha$, where $\alpha$ is a parameter ranging from 0 to 1.

5. The apparatus according to claim 1, wherein the parameter A is designated as $\alpha$ and the parameter B is designated as 0.5, where $\alpha$ is a parameter ranging from 0 to 1.

6. The apparatus according to claim 1, wherein the parameter A is designated as a known corresponding parameter in a table Ti and the parameter B is designated as $\alpha$, which ranges from 0 to 1, where the table Ti is a table established according to characteristics of users that correspond to the $i^{th}$ virtual channel, and the table Ti is established in advance according to parameters for adjusting a current ratio of the two adjacent electrodes, or according to a length ratio of the $i^{th}$ virtual channel to the two adjacent electrodes.

7. The apparatus according to claim 1, which is applied to a cochlear implant, a retinal prosthesis, a spinal cord stimulation apparatus, or a deep brain stimulation apparatus.

8. The apparatus according to claim 1, wherein the total power setting P is applied by an independent voltage source (V) or an independent current source (I).

9. A method for controlling electrical stimulation with a plurality of electrodes for stimulating nerve fibers, the method comprising:
   receiving a target stimulation location and level; and
   generating at least one parameter for adjusting power settings of an electrode set to be driven in an electrode array, so as to obtain a composite stimulation signal corresponding to a virtual channel of which a location and level match the target stimulation location and level;
   wherein the electrode set includes a first electrode, a second electrode, a third electrode and a fourth electrode, in which the second and third electrodes are adjacent and are of a first power polarity for controlling the location of the composite stimulation signal, while the first and fourth electrodes are of a second power polarity which is inverse with respect to the first power polarity, so as to balance the total power polarity of the electrode set and focus on a stimulation region of the composite stimulation signal, and
   wherein the second and third electrodes of the first power polarity have a power setting designated as $(-(1-A))P$ and $(-A)P$, respectively, while the first and fourth electrodes of the second power polarity have a power setting designated as $(B)P$ and $(1-B)P$, respectively, where A and B are parameters ranging from 0 to 1, the location of the composite stimulation signal can be controlled by adjusting the parameters A and B, and P is a total power setting.

10. The method according to claim 9, wherein the parameters A and B are designated so that they are equal to each other.

11. The method according to claim 9, wherein the parameters A and B are designated so that an equation, $A+B=1$, is fulfilled.

12. The method according to claim 9, wherein the parameter A is designated as 0.5 and the parameter B is designated as $\alpha$, where $\alpha$ is a parameter ranging from 0 to 1.

13. The method according to claim 9, wherein the parameter A is designated as $\alpha$ and the parameter B is designated as 0.5, where $\alpha$ is a parameter ranging from 0 to 1.

14. The method according to claim 9, wherein the parameter A is designated as a known corresponding parameter in a table Ti and the parameter B is designated as a ranging from 0 to 1, where the table Ti is a table established according to characteristics of users that correspond to the $i^{th}$ virtual channel, and the table Ti is established in advance according to parameters for adjusting a current ratio of the two adjacent electrodes, or according to a length ratio of the $i^{th}$ virtual channel to the two adjacent electrodes.

15. The method according to claim 9, which is applied to a cochlear implant, a retinal prosthesis, a spinal cord stimulation apparatus, or a deep brain stimulation apparatus.

16. An apparatus for controlling electrical stimulation used for stimulating nerve fibers, comprising:
an electrode array including an electrode set; and
an electrode controller for receiving input control signals and driving the electrode set in the electrode array so as to generate an composite stimulation signal in the electrode set;
wherein the electrode set comprises four electrodes each of which is separately powered and controlled by an independent power source, of which at least one electrode is of a first power polarity and other electrodes are of a second power polarity which is inverse with respect to the first power polarity, so as to balance a total power polarity of the electrode set and focus on a stimulation region of the composite stimulation signal, and
wherein power settings of the four electrodes are $(1-\alpha)AP$, $(2\alpha-1-\alpha B)P$, $(1-2\alpha+\alpha A-A)P$ and $(\alpha B)P$, respectively, where P is a total power setting, and $\alpha$, A and B are parameters ranging from 0 to 1.

17. The apparatus according to claim 16, wherein the parameters A and B are designated so that they are equal to each other.

18. The apparatus according to claim 16, wherein the parameters A and B are designated as 0.5.

19. The apparatus according to claim 16, which is applied a cochlear implant, a retinal prosthesis, a spinal cord stimulation apparatus, or a deep brain stimulation apparatus.

20. A method for controlling electrical stimulation with a plurality of electrodes for stimulating nerve fibers, the method comprising:
receiving a target stimulation location and level; and
generating at least one parameter for adjusting power setting of an electrode set to be driven in an electrode array, so as to obtain a composite stimulation signal corresponding to a virtual channel of which a location and level match the target stimulation location and level;
wherein the electrode set includes four electrodes each of which is separately powered and controlled by an independent power source, in which at least one electrode is of a first power polarity and other electrodes are of a second power polarity which is inverse with respect to the first power polarity, so as to balance a total power polarity of the electrode set and concentrate on a stimulation region of the composite stimulation signal, and
wherein power settings of four electrodes are $(1-\alpha)AP$, $(2\alpha-1-\alpha B)P$, $(1-2\alpha+\alpha A-A)P$ and $(\alpha B)P$, respectively, where P is a total power setting, and $\alpha$, A and B are parameters ranging from 0 to 1.

21. The method according to claim 20, wherein the parameters A and B are designated so that they are equal to each other.

22. The method according to claim 20, wherein the parameters A and B are designated as 0.5.

23. The method according to claim 20, which is applied to a cochlear implant, a retinal prosthesis, a spinal cord stimulation apparatus, or a deep brain stimulation apparatus.

* * * * *